United States Patent [19]

Mahar et al.

[11] Patent Number: 5,089,124
[45] Date of Patent: Feb. 18, 1992

[54] GRADIENT GENERATION CONTROL FOR LARGE SCALE LIQUID CHROMATOGRAPHY

[75] Inventors: Jeffrey T. Mahar, New Haven; Thomas C. Ransohoff, Fairfield; Adam H. Levin, Brookfield; Theodore Kettler, Ridgefield, all of Conn.

[73] Assignee: Biotage Inc., Charlottesville, Va.

[21] Appl. No.: 554,301

[22] Filed: Jul. 18, 1990

[51] Int. Cl.$^5$ .............................................. B01D 15/08
[52] U.S. Cl. ................................. 210/198.2; 210/101; 417/18; 417/20; 417/22
[58] Field of Search ................... 210/656, 101, 198.2; 55/386; 417/18, 20, 22, 53

[56] References Cited

U.S. PATENT DOCUMENTS

| | | | |
|---|---|---|---|
| 4,437,812 | 3/1984 | Abu-Shumays | 210/198.2 |
| 4,595,495 | 6/1986 | Yotam | 210/198.2 |
| 4,595,496 | 6/1986 | Carson | 210/198.2 |
| 4,879,029 | 11/1989 | Whitehead | 210/198.2 |
| 4,902,414 | 2/1990 | James | 210/198.2 |
| 4,919,595 | 4/1990 | Likuski | 210/198.2 |

Primary Examiner—Ernest G. Therkorn
Attorney, Agent, or Firm—Sheldon Parker

[57] ABSTRACT

Precise gradient control is accomplished using a high flow three-way valve, appropriate mixing, and precise metering control. Gradient elution profiles are generated for flow rates above 100 ml/min. Control involves precise selection of two solvents, and correction factors for valve lag times and pump/valve synchronizations. The gradient is controlled simultaneously with other non-timed operations through a single microprocessor controller.

5 Claims, 4 Drawing Sheets

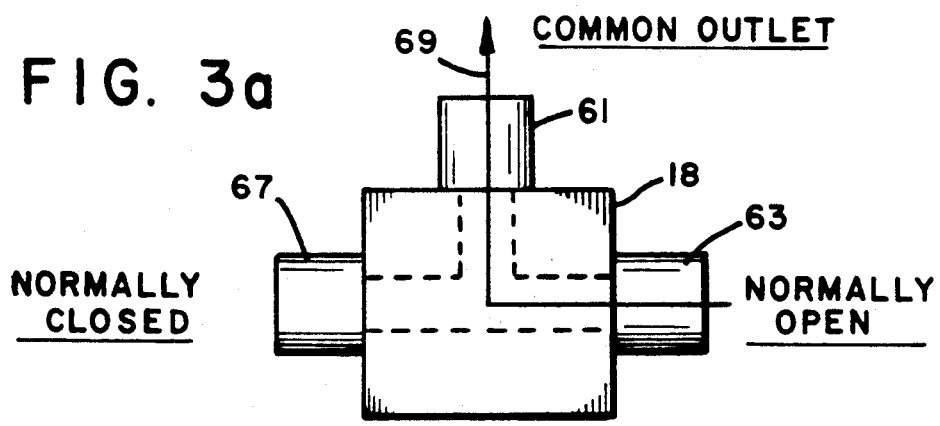
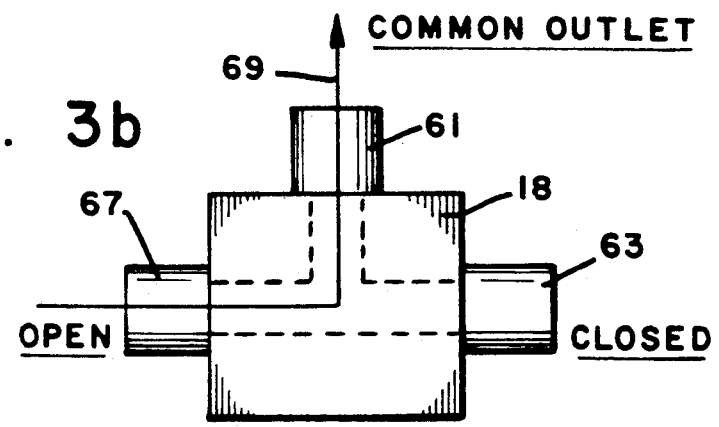
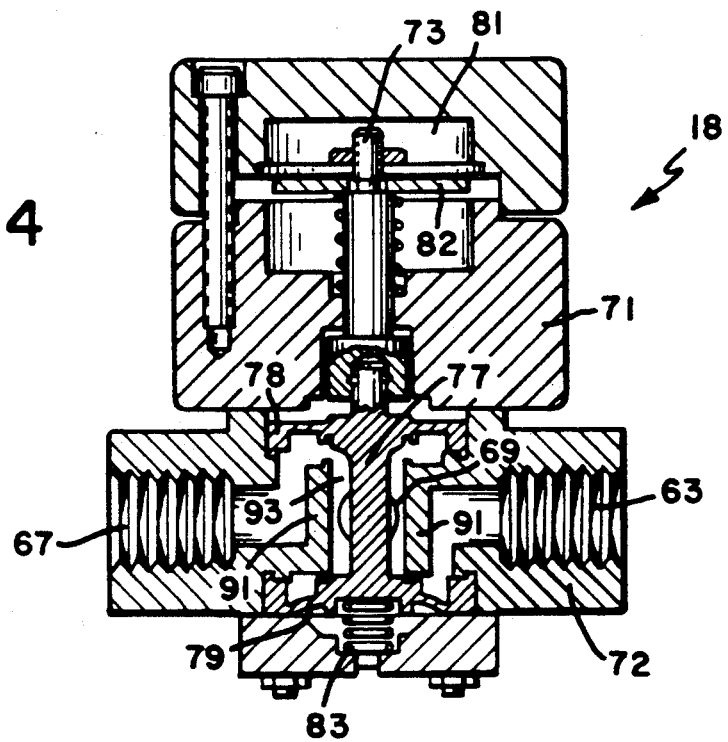

GRADIENT GENERATION CONTROL FOR LARGE SCALE LIQUID CHROMATOGRAPHY

FIELD OF THE INVENTION

This invention is directed to large scale liquid chromatography, and is particularly concerned with the precise mixing of liquid solvents in controlled proportions.

BACKGROUND OF THE INVENTION

In liquid chromatography a liquid sample is passed by a flowing stream of liquid solvent the mobile phase) through a column packed with particulate matter (the stationary phase). While passing through the column the various components in the sample separate from one another by adsorbing and desorbing from the stationary phase at different rates such that these individual components elute from the column at different times. The separated components then flow through a detector which responds to each component both qualitatively and quantitatively, thereby providing information to the user about the constituents of the sample.

Liquid chromatography systems often use mixtures of solvents or buffers as the mobile phase and, when operating in the gradient chromatography mode, the components of the mixture are changed over time.

Gradient generation has been an integral part of chromatography since its development. The precise metering and blending of the solvents has been optimized on an analytical scale (less than 1 ml/min), but has been only marginally successful on a large scale. The two main ways to meter solvents to perform gradients are classified as "high pressure", and "low pressure" approaches. High pressure gradient generation systems perform the mixing of the solvents on the outlet (high pressure) side of the pumps. Usually, each solvent is fed through an individual pump. Proportioning is controlled by varying flow rates of each pump for the correct proportions and mixing the two streams at a splitter. Drawbacks of this technique include:

1) Cost—The requirement of two pumps, or separate drive trains on the duplex or multi-headed pumps, is expensive. High pressure gradient systems require two pumps, each equal in capacity to the single pump used in a low pressure gradient system, to deliver 0 to 100% proportioning. Also, additional hardware is usually required, such as check valves to prevent over back-pressure on the alternate head or pump.

2) Performance—In generating gradients where one constituent proportion is less than 10%, efficiency of the pump decreases, causing inaccurate gradient profiles. The accuracy and precision of the proportioning is affected by motor speed and stroke length settings, especially with diaphragm and plunger-type pumps.

One advantage of high pressure gradient is that there is no risk to gradient performance due to pump and valve synchronization.

Low pressure gradient generation systems perform the mixing of the solvents at the inlet (low pressure) side of the pump. Only one pump is provided in the system to proportion two or more solvents. Valves at the inlet of the pump control the proportions of solvents. Mixing usually has been accomplished in the pump heads or at the pump outlet. Drawbacks of this technique include:

1) Valve/Pump Synchronization—Since of the diaphragm or plunger types have a stroking speed, and the valves have a cycle time for opening and closing, synchronization of operation will appear causing wave-like proportioning. Prior art systems used complicated algorithms (U.S. Pat. No. 4,595,496) to predict possible synchronizations.

2) Fine-Tuning—Because of differences in viscosity of many of the fluids used for proportioning, the valve and cycle times have to be fine-tuned for specific operations. Previous systems included a two-way valve for each solvent to be proportioned; however, accuracy is degraded when matched valves are used to proportion solvents of different viscosities.

3) Valve Lag Time—The difference in actuation time from one position to the other in a valve introduces a source of inaccuracy to the proportioning by the valve. This is an inherent characteristic of all valves.

4) Mixing—Better mixing is required for correct proportioning between solvents. Long cycle times required to accommodate lag time effects must be offset by large volume or high efficiency mixers.

The low pressure gradient system offers a low cost alternative to the high pressure system.

Recent examples of the prior art in this field are U.S. Pat. Nos. 4,437,812 and 4,595,496. The U.S. Pat. No. 4,437,812 describes a liquid chromatography system that uses a single reciprocating pump for gradient elution of components from a plurality of reservoirs where the pumping cycle comprises a plurality of fill strokes with intervening pumping strokes, With proportioning valves being used to admit the components according to a programmed ratio from particular reservoirs into the pump chamber during a given fill stroke.

The U.S. Pat. No. 4,595,496 patent employs a dedicated microprocessor to drive both a pump and fluid switching valves, and includes means for generating a ratio between the time to connect all of the reservoirs selected for actuation and the cycle time for a pump draw stroke. Selection of an appropriate ratio controls the relative phasing between the switching valve cycle and pump draw stroke such that the beginning of each switching valve cycle occurs at a different point of the pump draw stroke, thereby providing a desired averaging of the intake nonuniformities and producing more accurate solvent mixtures.

The U.S. Pat. No. 4,437,812 patent thus discloses a system which has the disadvantages of the necessity for fine tuning the pair of two-way valves in the system, wave proportioning as the result of pump/valve synchronization and an independent controller for gradient generation, while the system of the U.S. Pat. No. 4,595,496 patent has disadvantages in that 1) a large number of valve cycle times and pump cycle times with integer ratios must be eliminated from consideration; 2) there is a necessity for fine tuning the pair of two-way valves; and 3) an independent controller is needed for gradient generation in addition to the controller for remaining system process functions.

Thus it is apparent that while a substantial effort has been put forth to solve the problems in the field noted above, all efforts have thus far fallen short of providing an accurate, reproducible technique for metering liquids in controlled proportions with minimum cost and complexity in this field of large scale (100 ml/min or more) liquid chromatography.

SUMMARY OF THE INVENTION

Chromatography gradient operation is performed using a single three-way valve constructed to provide minimal pressure drop, a pump and a mixing device with gradient control effected using a relatively simple timing routine operable in conjunction with all other system process control functions on a single standard microprocessor. The three-way valve may be of the type actuated by air with spring return. In this case, compensation must be provided in gradient proportioning for the time lag due to spring return-speed/air venting.

With respect to the three-way valve, many problems encountered with the selection of valves for gradient control can be eliminated with high $C_v$ (low pressure drop) valves. A large orifice and high $C_v$ eliminates many of the pressure drops and inaccuracy commonly associated with attempts to proportion solvents of different viscosities. Minimum pressure drop allows relatively free flow and maintains accurate proportioning of solvents.

Regarding the metering pumps used, positive displacement pumps are widely used because of the outlet pressures encountered in chromatography (typically up to 6000 psig). Two positive displacement pumps used because of their excellent performance under high pressures are plunger and diaphragm pumps, where flow rate can be adjusted by stroke length and motor speed. Peristaltic pumps and rotary lobe pumps are also sometimes used.

Insofar as mixing is concerned, the blending of solvents from metering by the three-way valve is accomplished by mixing in the pump heads, from the dead volume in the system, using a mixing device such as a static mixer, or during flow through the chromatographic column.

The proportioning in this invention is accomplished by cycling the three-way valve by time. Cycling the valve will generate a portion of one solvent followed by a portion of another solvent. An in-line mixer, the hold-up volume of the system, or the heads will blend the solvents into a consistent mixture. Valve cycle control can be accomplished via a microprocessor-based system e.g., programmable logic controller, personal computer, etc.). Four potential problems encountered in proportioning using three-way valves and their resolution by this invention are described below:

a) Lag Time—For valves using an air impulse to open, spring to close actuation, or vice versa, there is a significant amount of time required for the valve to return to the initial position. The lag time is associated with the spring returning and the release of air pressure. The "initial" position is one in which a designated valve inlet is normally open to flow from the reservoir associated therewith.

In the present invention, to reduce the lag time, a quick exhaust valve mounted on the proportioning valve releases the air pressure near the valve instead of at the air source. Even with the quick exhaust, minimum lag times seen with spring return in air-actuated valves are around 200 milliseconds. Air actuation of the valve normally has a quick response.

The lag time in the proportioning of solvents is compensated for by programming the microprocessor as follows: If Solvent A is in the normally open port and Solvent B is in the normally closed port, correct proportioning is obtained by subtracting the amount of time the valve is left open in the "B" port. For example, in a cycle time of 10 seconds and a lag time of 200 ms, a 50/50 proportion, as set by the computers, has the "A" port open for 5.0 seconds and "B" port open for a signal duration of 4.8 seconds, thereby allowing for the 200 ms mechanical lag of spring return.

b) Pump/Valve Synchronization—If a pump controlled by stroking speeds, such as a diaphragm or plunger pump, and a valve cycling by time for proportioning are used in conjunction, there are stroking speeds and cycle time multiples where synchronization can occur. Pump/valve synchronization produces inconsistent gradient profiles causing unreliable chromatographic results. Historically, U S. Pat. No. 4,595,496, determined all possible stroking speeds and cycle time multiples where synchronizations may occur and eliminated them as setpoints in their programming routines. Permutations could be in the hundreds.

In the present invention, a constant is determined empirically for each of several ranges of pump speeds at which synchronization with valve cycle time does not occur. For any given range of pump speeds the constant then defines the allowable cycle times according to the formula Constant = (pump speed, %) (valve cycle time, seconds)

For example, if the combination of 10 second cycle time and 100 percent pump speed is found not to generate synchronization, the Constant 1000%-seconds will have been determined. If the pump speed is then changed to 80%, then the new cycle time for non-synchronization is 12.5 seconds.

c) Mixing and Accuracy—Once the solvents are proportioned, the solvents have to be blended into a consistent mixture. The hold-up volume from the point of proportioning to the column inlet should be minimized to reduce the time required to obtain the desired composition when proportioning is changed. Shorter cycle times allow smaller mixing devices and/or less hold-up volume in the systems. The Constant described above will be dependent on the required cycle time range. Cycle times can be decreased to reduce the amount of mixing needed and therefore the size of any mixer required. The control has a lower limit of actuation to 5 ms portions so proportioning of less than 1% can be obtained.

d) Microprocessor Control—Some large scale chromatographic operations use a microprocessor controller for gradient operations and another microprocessor controller for other process control operations. Multiple microprocessors for various controls may be difficult and confusing to integrate, expensive, and not very flexible.

Since the gradient profile is a timed routine, a more cost-effective method of proportioning valve control is to utilize hardware timers, available on many microprocessor-based systems.

A number of timer chips are typically available to use for gradient operations, or for other timed operations which must be controlled in parallel with time-independent system control functions. Such time-independent functions would include valve actuations, pump control and manipulation of outgoing and incoming field signals.

In this design, the gradient is set up through an operator interface or downloaded from a remote computer. The gradient timing routines are operated in the background via the timer chip. When the gradient valve or system pump requires control, a hardware or software interrupt is generated allowing the microprocessor to perform those control functions and return rapidly to the master control program.

Chromatography systems and equipment in accordance with the present invention find application in the clinical testing and production of pharmaceuticals and biotechnology products, as well as in the analysis and production of fine chemicals and specialty chemicals.

DESCRIPTION OF THE DRAWINGS

FIGS. 3a and 3b are schematic representations of the three-way valve employed in the present invention;

FIG. 4 is a more detailed illustration in section of a typical three-way valve employed in the present invention.

DETAILED DESCRIPTION

Figure 1:
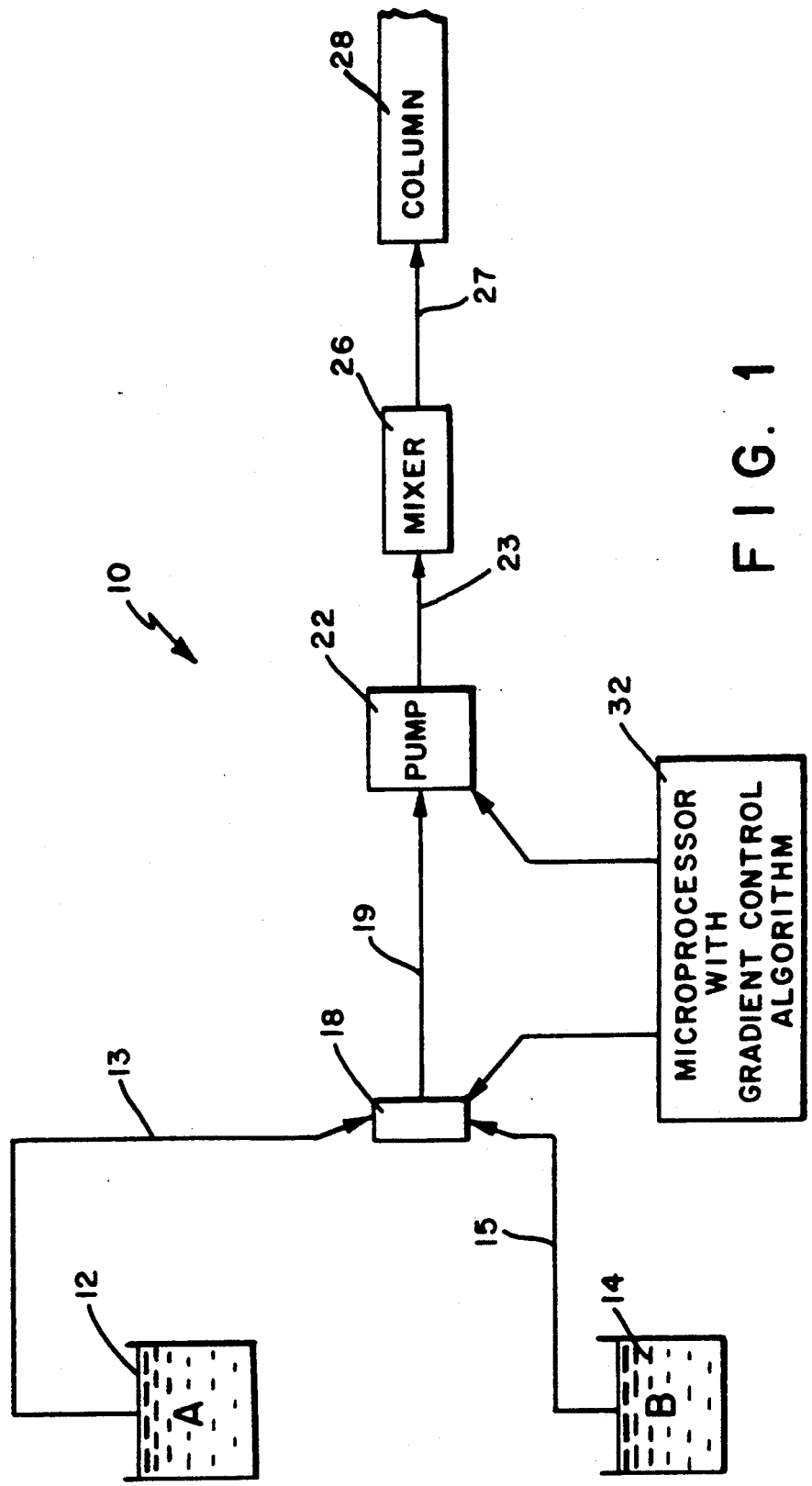
FIG. 1 is a schematic representation of the solvent flow scheme of the invention.

Referring to the figures, in FIG. 1 a flow diagram 10 illustrates the formation and supply of a gradient mobile phase to a chromatography column. Thus, a pair of reservoirs 12 and 14 each contain a quantity of solvents A and B. Reservoir 12 is connected to the three-way gradient valve 18 by a conduit 13 while reservoir 14 is connected to the gradient valve by the conduit 15. The outlet of the gradient valve 18 is connected to the pump 22 by the conduit 19 and the outlet of pump 22 is connected to the mixer 26 by the conduit 23. The mixer 26 feeds into the chromatography column 28 through conduit 27.

Figure 2:
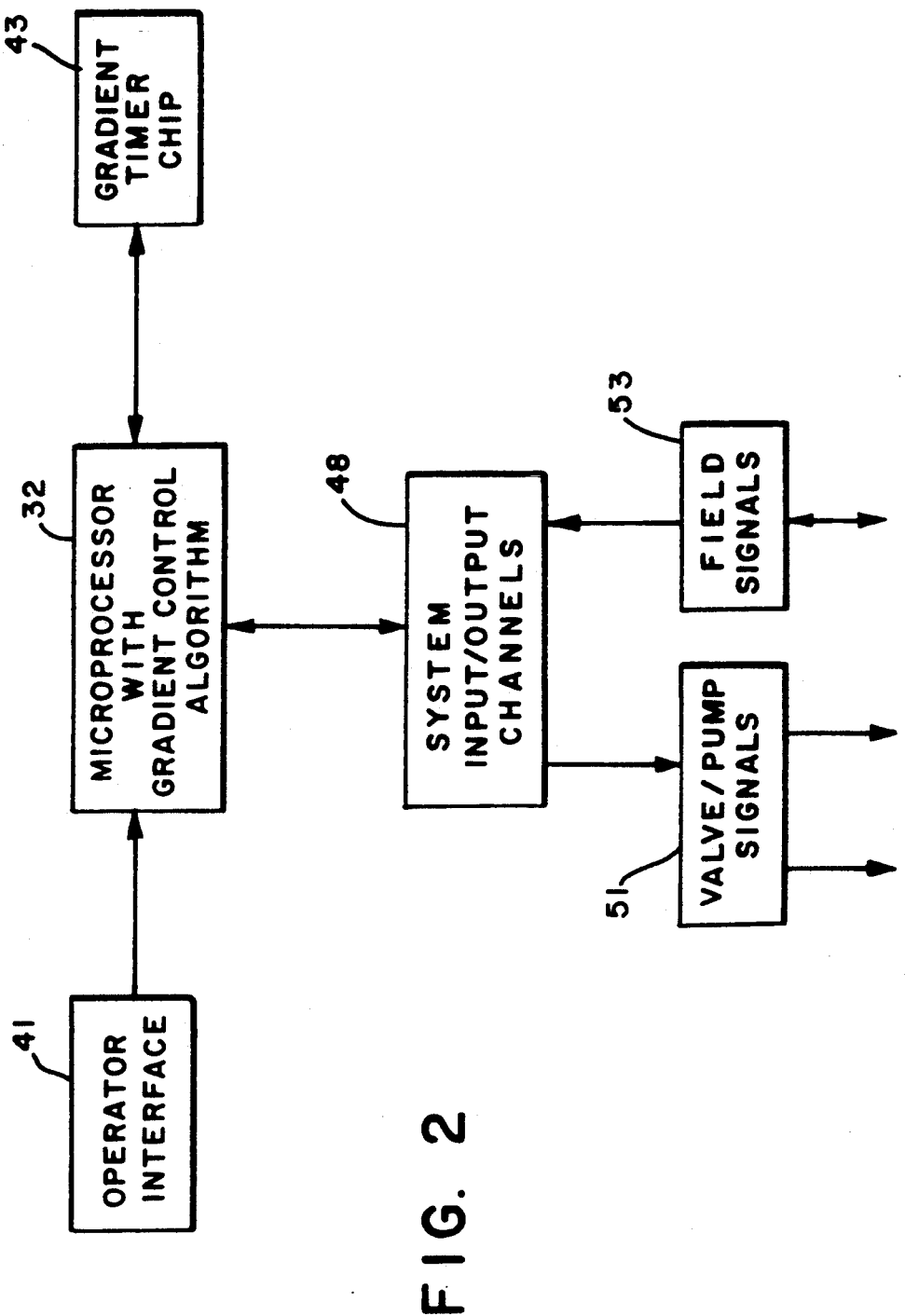
FIG. 2 is a block diagram of the system for gradient control with other process control.

The control system illustrated in FIG. 2 controls the gradient production as well as other functions such as accepting and recording data generated by the chromatography column. The operator interface 41 typically includes a keyboard and monitor for introducing instructions into the microprocessor 32 which is provided with a gradient control algorithm and a gradient timer chip 43. By means of this timer chip, control of the gradient valve is hardware or software interrupt driven by the microprocessor thereby allowing gradient control and other system functions to be controlled simultaneously. Through the system input/output channels 48, microprocessor control 32 for the gradient valve and pump operation 51, which includes other system valves and pumps, is essentially operated simultaneously with field signal control 53 for other process operations such as accepting and recording data from the chromatography column and other valve and pump controls.

In FIGS. 3a and 3b, a highly simplified schematic representation of the three-way gradient valve 18 is shown. The gradient valve has a pair of inlets 63 and 67 and a common outlet 61. The inlets 63 and 67 are connected to reservoirs containing the solvents to be proportioned.

In FIG. 3a, the arrow 69 shows flow from one of the reservoirs through the normally open inlet 63 to the outlet 61 while the inlet 67 is normally closed.

In FIG. 3b, the arrow 69 indicates flow from the other of the reservoirs through inlet 67, now open, to the common outlet 61 while the inlet 63 is closed.

Turning now to FIG. 4, there is illustrated in section an air-actuated three-way valve of a type which is found to be useful in the present invention The valve body 72 is surmounted by an air actuation housing 71 which has therein an air chamber 81. Mounted for vertical movement therein is a plunger 73 which has mounted thereon a cylinder 82 which closely fits within the walls of the air chamber 81. It will be noted that introduction of air at elevated pressure into air chamber 81 above the cylinder 82 will cause the plunger 73 to move downwardly. The valve body 72 has a pair of inlets 63 and 67 and an outlet 69. A valve stem 77 is provided between inlets 63 and 67 and has mounted thereon a pair of diaphragms 78 and 79 adjacent the top and bottom of the valve stem. An inner wall 91 surrounds but is spaced from the valve stem 77. The space 93 about valve stem 77 constitutes a liquid passageway which is in communication with the valve outlet 69. The valve stem 77 is capable of vertical movement between the two extreme positions in which the diaphragms 78 and 79 can alternately be seated against the wall member 91. As shown, the valve stem in its uppermost position as urged by the spring member 83 and the diaphragm 79 is thereby sealed against the lower end of wall member 91. At the same time, the upper-most diaphragm 78 is not sealed against the upper-most portion of wall 91 and thereby permits flow of liquid from inlet 67 to outlet 69. Upon air actuation of the valve, the plunger 73 is driven downwardly contacting valve stem 77 and moving it downwardly against the resistance of spring 83. The diaphragm 78 thereby comes into contact with the upper extremity of wall 91 sealing off contact between inlet 67 and outlet 69 and at the same time moving diaphragm 79 downwardly thereby opening the passage between inlet 63 and outlet 69 to permit the second liquid to flow through outlet 69. Upon venting of the air from air chamber 81, the valve stem 77 will move upwardly under the influence of spring 83 and also moving the plunger 73 to its upper position once again sealing off inlet 63 from the outlet 69 and permitting inlet 67 to have access to outlet 69.

It will be appreciated that the character of the response of the mechanism to air actuation is different from that of the response to the spring return. These differences may affect the precision of opening and closing of the valve.

As a demonstration of gradient accuracy of the system of the invention, gradient runs were performed and recorded. The test conditions under which the gradient runs were performed are described in Table I below:

TABLE I

| GRADIENT TEST CONDITIONS | |
|---|---|
| A Solvent | Water |
| B Solvent | 99% Water/1% Acetone |
| Detection | Ultraviolet Detector No. 1: 254 nm |
|  | Ultraviolet Detector No. 2: 280 nm |
| Chart Speed | 5 mm/min |
| Flow Rate | 300 ml/min |
|  | Stroking Length: 20 mm |
|  | Stroking Speed: 68 spm |
| Pressure | 500 psig |

Under the conditions specified in Table I, a descending step gradient was programmed to decrease solvent composition in 10% B solvent steps starting from 100% B solvent. Each step was held for 2 min. before descending to the next step until 0% B solvent was attained. This descending step gradient program is set forth in Table II below:

TABLE II

DESCENDING STEP GRADIENT PROGRAM

| NO. | TIME (min) | FLOW (ml/min) | % A Solvent | % B Solvent |
|---|---|---|---|---|
| 1 | 2.0 | 300 | 10.0 | 90.0 |
| 2 | 4.0 | 300 | 20.0 | 80.0 |
| 3 | 6.0 | 300 | 30.0 | 70.0 |
| 4 | 8.0 | 300 | 40.0 | 60.0 |
| 5 | 10.0 | 300 | 50.0 | 50.0 |
| 6 | 12.0 | 300 | 60.0 | 40.0 |
| 7 | 14.0 | 300 | 70.0 | 30.0 |
| 8 | 16.0 | 300 | 80.0 | 20.0 |
| 9 | 18.0 | 300 | 90.0 | 10.0 |
| 10 | 20.0 | 300 | 100.0 | 0.0 |

In Table III information related to an actual test run is set forth. In the first column, the programmed values of the gradient are set forth. In the second column, the predicted readings are set forth for the ultraviolet detector at the 254 nm wave-length level using the formula below Table III after actual readings at 100% B and 0% B and assuming a linear relationship. In the third column, the actual readings obtained by the ultra-violet detector at the 254 nm wave-length at each step are given.

Similar information is offered in Table III with respect to the ultraviolet detector with a 280 nm wave-length value. The equations below the table present the method for obtaining the predicted values for each ultraviolet detector.

TABLE III

GRADIENT TEST RESULTS

| Prog. Comp. | Ultraviolet Detector 254 nm | | Ultraviolet Detector 280 nm | |
|---|---|---|---|---|
| % B | Predicted | Actual | Predicted | Actual |
| 100 | 99.0 | 99.0 | 100.0 | 100.0 |
| 90 | 89.2 | 89.5 | 90.1 | 90.5 |
| 80 | 79.3 | 79.5 | 80.2 | 80.0 |
| 70 | 69.5 | 70.0 | 70.3 | 70.0 |
| 60 | 59.6 | 60.0 | 60.4 | 60.5 |
| 50 | 49.8 | 50.0 | 50.5 | 50.5 |
| 40 | 39.9 | 40.0 | 40.6 | 40.5 |
| 30 | 30.1 | 30.5 | 30.7 | 31.0 |
| 20 | 20.2 | 20.5 | 22.0 | 21.0 |
| 10 | 10.4 | 10.5 | 12.0 | 11.0 |
| 0 | 0.5 | 0.5 | 1.0 | 1.0 |

254 nm: Predicted = 0.99 × (Programmed Comp. % B) + 1.0
280 nm: Predicted = 0.985 × (Programmed Comp. % B) + 0.5

Figure 5:
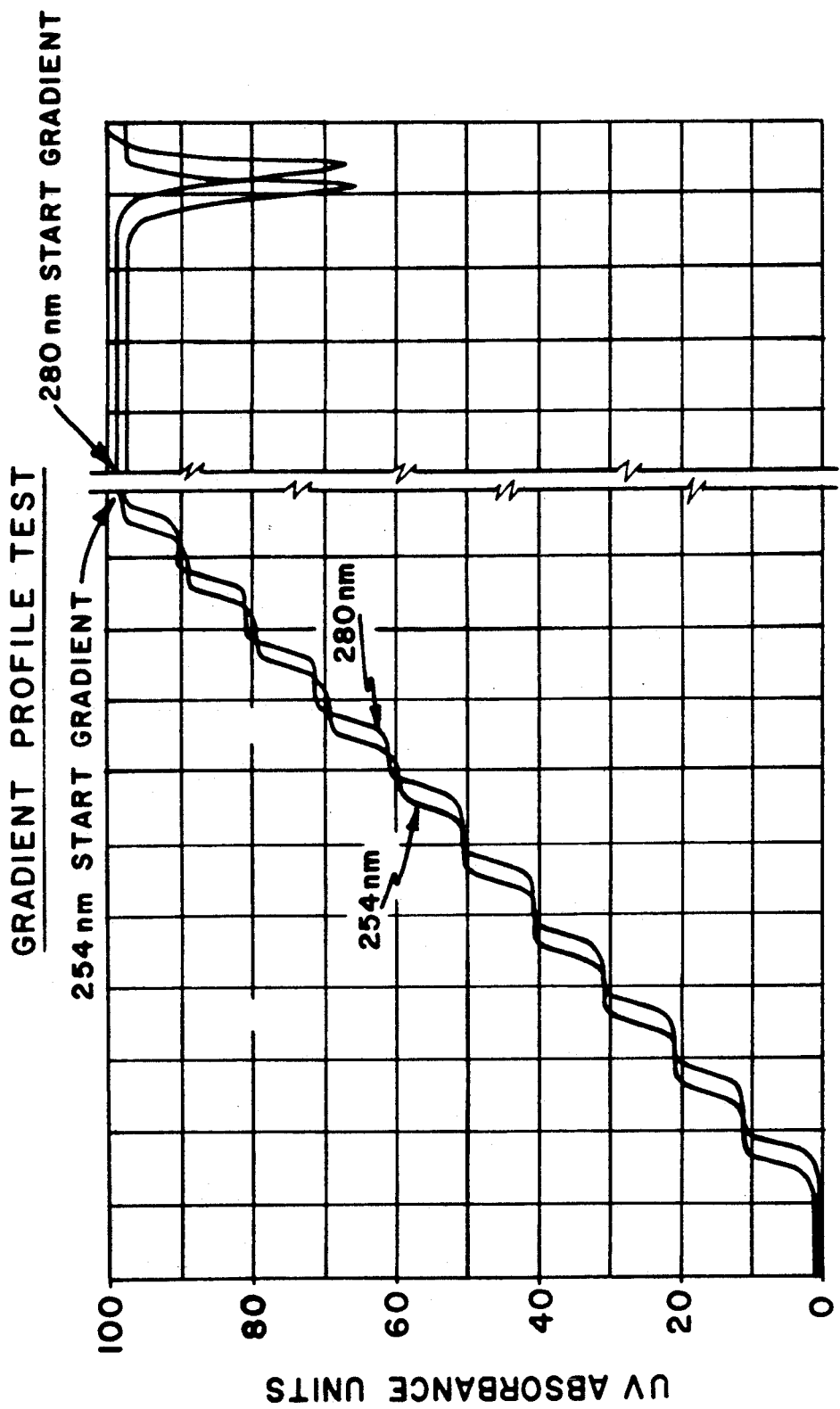
FIG. 5 is an illustration of a chromatograph produced in one example of a process according to the invention.

In FIG. 5 may be seen a representation of the actual chart from which the data of Table III was taken which further demonstrates the remarkable accuracy of the system of the invention in obtaining desired compositions over a wide range of compositional levels. In this Figure, the starting point for the descending step gradient for the detectors at each wave-length are indicated by arrows at the top of the chart.

It should also be noted that similar accuracy has been achieved in ascending step gradient test runs, as well as in linear test runs.

We claim:

1. A large scale liquid chromatography system comprising:
   a column;
   a pair of reservoirs each containing a liquid to be mixed together in desired proportions to form a mobile phase;
   a single three-way valve means having a hi $C_v$ value and large orifices with a pair of inlets each connected to one of said reservoirs and a single valve outlet;
   said valve means having an initial position in which a first valve inlet is open to a first of said reservoirs and a second spring return position which opens a second valve inlet to a second of said reservoirs while closing said first valve inlet;
   a pump having an inlet and an outlet for conveying liquid over a range of flow rates to said column;
   a delivery flow conduit connecting said single valve outlet to said pump inlet;
   means for effecting cycling of the opening of said pair of valve inlets to achieve said desired proportions in said mobile phase;
   said means capable of adjusting pump speed and valve cycle time to avoid wave-like proportioning due to pump/valve synchronization effects in accordance with the formula $$C = (\text{pump speed, \%}) (\text{valve cycle time, seconds})$$

wherein C is a constant determined empirically by observation of pump speeds and valve cycle times at which pump/valve synchronization does not occur.

2. The liquid chromatography system of claim 1 wherein said means is a microprocessor controller which also corrects inherent valve lag time by adjusting signal duration for controlling flow from at least one of said reservoirs, said microprocessor controller simultaneously controlling other system functions of said liquid chromatography system.

3. The liquid chromatography system of claim 1 in which said three-way valve has an initial air-actuated first position in which a first valve inlet is open to a first of said reservoirs and a second spring return position which opens a second valve inlet to a second of said reservoirs while closing said first valve inlet.

4. The liquid chromatography system of claim 3 in which said three-way valve exhibits a significant lag time for return to normally open first position associated with spring return operation and release or venting of air pressure and wherein said means is a microprocessor controller which selectively activates said valve to said air-actuated open position to admit liquid from one of said reservoirs to said pump inlet and initiates air venting from said valve to facilitate spring return of said valve to open said second valve inlet to allow flow from said second reservoir in a desired proportion, said microprocessor controller correcting for the lag time error by decreasing signal duration for said second reservoir by an amount of time equal to the delay in return to the initial position caused by the slow spring actuation, said microprocessor controller simultaneously controlling other system functions of said liquid chromatography system.

5. A large scale liquid chromatography system comprising:
   a column,
   a pair of reservoirs each containing a liquid to be mixed together in desired proportions to form a mobile phase, a single three-way gradient valve means with a $C_v$ value greater than 1.0 having a pair of inlets and a single outlet, flow conduits connecting each reservoir to one of said valve inlets, a pump having an inlet and an outlet for conveying liquid over a range of flow rates in excess of 100 ml/min to said column, a delivery flow conduit connecting said single valve outlet to said pump inlet, said valve having an air-actuated initial position in which a first valve inlet is open to a first of said reservoirs and a second spring return position which opens a second valve inlet to a second of said reservoirs while closing said first valve inlet, said valve exhibiting a significant lag time for return to said initial position associated with the spring return and release of air pressure, a microprocessor having a timer chip wherein control of said gradient valve means is hardware or software interrupt driven by the microprocessor to allow gradient control while other system functions are controlled simultaneously said microprocessor, said microprocessor selectively activating said valve to said air-actuated open position to admit liquid from one of said reservoirs to said pump inlet and for venting air from said valve actuator to facilitate spring return of said valve means to open said second valve inlet to allow flow from said second reservoir in a desired proportion, said microprocessor means correcting for the lag time error by decreasing signal duration time for said second reservoir, said microprocessor adjusting pump speed and cycle time to avoid wave-like proportioning in accordance with the formula $$C = (\text{pump speed, \%}) (\text{valve cycle time, seconds})$$

the value C having been determined empirically by observation and said microprocessor simultaneously controlling other system functions of said liquid chromatography system.

* * * * *